(12) United States Patent
Von Eichel-Streiber et al.

(10) Patent No.: US 7,700,091 B2
(45) Date of Patent: *Apr. 20, 2010

(54) MODIFIED BACTERIA AND METHODS OF USE TO TRANSFORM EUKARYOTIC CELLS

(76) Inventors: Christoph Von Eichel-Streiber, Bingerweg 15, D-55444, Schweppenhausen (DE); Trinad Chakraborty, Seltersweg 85, D-35394, Giessen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/894,438

(22) Filed: Jul. 19, 2004

(65) Prior Publication Data

US 2005/0042755 A1 Feb. 24, 2005

Related U.S. Application Data

(62) Division of application No. 09/581,005, filed as application No. PCT/EP98/08096 on Dec. 11, 1998, now Pat. No. 6,825,028.

(51) Int. Cl.
| | |
|---|---|
| A61K 48/00 | (2006.01) |
| A61K 31/70 | (2006.01) |
| A01N 63/04 | (2006.01) |
| A01N 65/00 | (2006.01) |
| A01N 43/04 | (2006.01) |

(52) U.S. Cl. .................. 424/93.2; 424/93.3; 424/93.45; 514/44 R

(58) Field of Classification Search .................. None
See application file for complete search history.

(56) References Cited

U.S. PATENT DOCUMENTS 5,877,159 A 3/1999 Powell
6,825,028 B1 * 11/2004 Von Eichel-Streiber et al. .. 435/252.3

FOREIGN PATENT DOCUMENTS

| WO | WO 96/34631 | 11/1996 |
|---|---|---|
| WO | WO 97/08955 | 3/1997 |
| WO | WO 9708955 A1 * | 3/1997 |

OTHER PUBLICATIONS

Higgins, et al. (1998) Nature Biotechnol., 16: 138-39.*
Courvalin, et al. (1995) C.R. Acad. Sci. III, 318(12): 1207-12: Abstract Only.*
Weiss, et al. (2001) Curr. Opin. Biotechnol., 12: 467-72.*
Goossens, et al. (1995) Int. Immunol., 5(7): 797-805.*
Sullivan, et al. (1997) J. Biol. Chem., 272(29): 17972-80.*
Park, et al. (1990) Gene, 94(1): 129-32.*
DW Pascyak et al., Behring Inst. Mittl, Oral Bacterial Vaccine Vectors for the Delivery of Subunit and Nucleic Acid Vaccines to the Organized Lymphoid Tissue of the Intestine,: 1997, 98, pp. 143-152, Pascual, et al.
C Grillot-Courvalin et al., Nature Biotechnology, "Functional gene transfer from intracellular bacteria to mammalian cells," Sep. 1998, vol. 16, pp. 862-866.
G. Ditrich et al., Nature Biotechnology, "Delivery of antigen-encoding plasmid DNA into the cytosol of macrophages by attenuated suicide *Listeria monocytogenes*," Jan. 1998 vol. 16.
Bryner et al., Research on listeriosis in milk cows with intramammary inoculation of *Listeria monocytogenes*. Acta Microbiologica Hungarica. 1989, vol. 36, Nos. 2-3, pp. 137-140.
Goossens et al., Attenuated *Listeria monocytogenes* as a live vector for induction of CD8+ T cells in vivo: a study with the nucleoprotein of lymphocytic choriomeningitis virus International Immunology. 1995, vol. 7, No. 5, pp. 797-805, Goosens, et al.
D.A. Saltzman et al., Cancer Biother Radiopharm (1996) 11 (2) pp. 145-153, Attenuated *Salmonella typhimurin* containing interleukin-2 decreases MC-38 hepatic metastasi: a novel (PubMed Accession No. 10851531).
Saltzerman, et al (1996) Cancer Biother and RadioPharm., 11(2) pp. 145-153.
Biosis BA 70: 30266/DN (Abstract of: Schaffner, W., PNAS 77, 1980, 2163-7).
Lety, et al., 2006, Microbiol. 152: 1287-96.
Lety, et al., 2003, Microbiol. 149: 1249-55.
Auerbuch, et al., 2001, Infect. Immunol. 69: 5953-57.
Smith, et al., 1996, J. Cell Biol. 135: 647-60.
Lauer, et al., 2001, Mol. Microbiol. 42: 1163-77.

* cited by examiner

*Primary Examiner*—Robert M Kelly
(74) *Attorney, Agent, or Firm*—Patent Central LLC; Stephan A. Pendorf; Katherine Dover

(57) ABSTRACT

The present invention concerns a TGC method for inducting targeted somatic transgenesis in an animal host, whereby bacteria with a foreign DNA integrated into an episomal vector release, under the control of eukaryotic regulatory elements forulterior transcription and expression, said foreign DNA in the case of infection of a foreign organism, organ, tissue, cell line or individual cells, causing transcription and expression of foreign DNA and/or foreign protein in said location.

13 Claims, No Drawings

MODIFIED BACTERIA AND METHODS OF USE TO TRANSFORM EUKARYOTIC CELLS

CROSS REFERENCE TO RELATED APPLICATIONS

This application is a Divisional Application of U.S. application Ser. No. 09/581,005, filed Jun. 6, 2000, now U.S. Pat. No. 6,825,028 allowed on Apr. 19, 2004, which is a national stage of PCT/EP98/08096 filed Dec. 11, 1998, and is based upon German Patent Application No. DE 19754 938.1 filed Dec. 11, 1997, and which are hereby incorporated in their entirety by reference.

The object of the invention is a method for inducting targeted somatic transgenesis (TGC=targeted genetic conditioning), which is used for expressing foreign proteins in cells, tissue, organ or an entire host organism, as well as for somatic gene therapy.

It is known that proteins for technical application or for therapeutic purposes can be expressed in sufficient quantity by the transfer of genes in microorganisms or mammalian cells. These procedures are particularly important for proteins occurring naturally in the body, such as hormones, regulatory factors, enzymes, enzyme inhibitors and humanized monoclonal antibodies which are otherwise only available to a limited extent or not available at all. The procedures are also important for producing surface proteins of pathogenic microorganisms or viral envelope proteins so as to safely produce diagnostic tests and for the development of efficacious vaccines. Through protein engineering it is also possible to produce new types of proteins, which through fusion, mutation or deletion of the corresponding DNA sequences, have properties optimized for particular uses, for example immunotoxins.

Genes obtained from human cells are also functional in mouse, rat or sheep cells and there lead to the formation of corresponding gene products. This has already been made use of in the production of therapeutic products, for example in the milk of transgenic farm animals. The hitherto known method has been by the microinjection of corresponding foreign DNA carrying vectors into the nucleus of the fertilized egg cell, in which the DNA is then incorporated into the chromosome with a yield of 1%. The transgenic fertilized egg cell is then transplanted into hormonally stimulated mother animals. An offspring carrying the transfected gene in all its body cells is the basis for the creation of a "transgenic herd/flock". Using gene technology it is now possible to alter farm animals in such a targeted way that they produce human proteins in their blood, tissue or milk, which cannot be produced by microorganisms or plants.

However, the use of transgenic animals as protein production factories has the decisive disadvantage that it is necessary to manipulate the germ line of the animal. Due to the considerable expenditure of technology and time required to create and breed transgenic animals and also due to the discussions regarding the ethical consequences of these methods, alternative methods for producing proteins in animal hosts without manipulation of the germ line are necessary and would be very advantageous.

It is known, furthermore, that the milk of mammals such as cows, sheep, goats, horses or pigs can contain a range of disease-causing bacterial agents. Among such agents are *Listeria, Mycobacteria, Brucella, Rhodococcus, Salmonella, Shigella, Escherichia, Aeromonads* and *Yersinia* or general bacteria with intracellular lifestyle [1, 2]. These bacteria are usually transmitted to humans or animals through oral ingestion [3], but can also be transmitted by droplet infection. A major source for the infection of humans with *Listeria* [4], *Mycobacteria* [5] and *Escherichia coli* is contaminated milk [6]. Humans ingest the bacteria when consuming unpasteurised milk or milk products. The other bacteria types listed above, such as *Salmonella, Shigella, Yersinia, Rhodococcus* and *Brucella* are transmitted to humans in a similar way. However, bacteria may also enter humans through other bacterially infected animal products from cows, goats, sheep, hares, horses, pigs or poultry.

The infection of animals frequently occurs through mucosal surfaces and very frequently through the digestive tract. However, after ingestion of bacteria, for example in the case of *Listeria*, not all tissues show symptoms of infection. In cows and goats the infection is mainly evident in the udder, spleen and liver. In sheep there may additionally be illness in the central nervous system in the form of meningitis, so not all animals survive the infection. With infection of the udder, the infection chain is closed. With contaminated milk, acquired bacteria can reinfect another animal, for example a suckling calf or a human via the digestive tract.

The following is known at present regarding the process of bacterial infection in humans, here presented using the example of *Listeria*:

Of the six known *Listeria* species, only *L. monocytogenes* and *L. ivanovii* are pathogenic for humans [7]. Illness in humans results from consuming infected milk or milk products. The course of the illness depends on the state of health of the individual and is generally inapparent. Intrauterine transmission of bacteria to the fetus may occur during pregnancy, resulting in abortion, stillbirth or premature birth. In all cases excellent and problem-free treatment exists using antibiotics such as ampicillin or erythromycin [8; 8a].

The mode of entry into the cell occurs is well defined for *L. monocytogenes* in humans and animals and for *L. ivanovii* in sheep. For full pathogenicity of *Listeria* to occur, a range of pathogenicity factors are necessary. Among them are PrfA (positive regulator of virulence), ActA (actin nucleating protein), PlcA (phosphatidylinositol-specific phopholipase), PlcB (phosphatidylcholine-specific phopholipase), Hly (listeriolysin), Mpl (metalloprotease) [9]. The cell specificity of the pathogen—host cell interaction is mediated through a range of proteins. Among these are the internalins InlA and InlB, which are involved in the initial contact and the interaction of bacteria and cell surface [10, 11]. Under experimental conditions *L. monocytogenes* can also infect endothelial cells, epithelial cells, fibroblasts and hepatocytes. In addition, *L. monocytogenes* can infect cells of the white blood cell count like neutrophilic granulocytes, macrophages and lymphocytes. This is a significant factor in the transmission of bacteria from the site of primary infection to the target organ in the host. Finally, lung tissue can also be infected by *Listeria* if the bacteria are applied as a droplet infection.

After adhering to the cell surface, *L. monocytogenes* is taken up by the cell by endocytosis, the bacterium breaks down the endosome membrane under the effect of listeriolysin (Hly) and is thus released into the cell cytosol [14]. Once inside the cell, the bacteria can proliferate. With the production of further proteins, the fully pathogenic bacterium does not stay localized but actively spreads to distal sites. Bacterial spread is effected by using a range of proteins from *L. monocytogenes* itself and some cellular proteins [15, 16]. ActA is expressed on the cell surface of *L. monocytogenes*. It binds the cellular protein VASP, which for its part forms the bridge required for the attachment of cellular actin. Actin tails subsequently develop which carry the bacterium at their tip and thus move it further through the cell. If *L. monocytogenes* contacts the cell membrane, a membrane protrusion forms, which projects directly into any adjacent cells if they are present. This protrusion is then endocytosed by the adjacent cell so the *L. monocytogenes* is then inside the new cell within a double membrane. The two membranes are dissolved under the effect of Hly and PlcB [17]. At the end of this process *L. monocytogenes* has also infected the neighbouring cell and the infection process begins again. In this way *L. monocytogenes* enters, for example, secretory cells of the cow udder. Secreted *Listeria* proteins are detectable in milk, i.e. they are passed on intracellularly from the lactating cell into the milk [18]. Hly (listeriolysin) and IrpA (internalin related protein [19]) are two pathogenicity factors belonging to this group of proteins which are produced, secreted and passed out in milk in large quantities by *L. monocytogenes* [20].

Knowledge of the infection process has made it possible to alter *L. monocytogenes* genetically in such a way that it expresses foreign proteins. Examples for the expression of foreign proteins in *L. monocytogenes* are: alkaline phosphatase from *Escherichia coli*, nucleoprotein from influenza virus, major capsid protein (L1) from cottontail rabbit papillomavirus (CRPV) and Gag protein from HIV type 1 [20 to 27].

In addition to proteins of prokaryotic origin, this also applies to viral proteins which are not normally produced within eukaryotic cells. These viral proteins and similar foreign proteins of prokaryotic and eukaryotic origin can be produced by *L. monocytogenes* without a eukaryotic cell being needed. Proteins produced by *L. monocytogenes* are secreted into the milk.

Infection by bacteria occurs through specific interactions of ligand proteins of the bacteria with receptor proteins of the target cells. In the case of *L. monocytogenes,* the internalin family plays a significant role; the internalin proteins determine to a large extent the cell specificity of the infection process [28]. Additionally, an ActA dependent cell ingestion has been discussed, which is mediated through receptors of the heparan sulphate family [29]. If *L. monocytogenes* infects a cell, it does not lead to a full infection cycle in every case. If listeriolysin in *L. monocytogenes* is inactivated, the bacteria then remain in the endosome and the infection in the "first cell" does not take place. Bacteria in which the protein ActA is deleted, inactive or no longer available, enter the first infected cell but remain there and can no longer infect the neighbouring cells [30, 31]. If PclB is deleted, the bacteria are no longer able to establish itself in the second cell.

*L. monocytogenes* is a bacterium which can be treated with a range of antibiotics. Ampicillin and penicillin (always in combination with gentamycin) are particularly suitable. Erythromycin and sulphonamides can also be used as alternatives. Tetracycline, vancomycin or chloramphenicol can also be used in special cases [32]. Similar treatments exist for other bacteria [8a] of the following types: *Aeromonads, Bartonella, Brucella, Campylobacter, Enterobacteriaceae, Mycobacterium, Renibacterium, Rhodococcus* and other bacteria which are genetically or biochemically related to them.

Given this information, the question arises as to how bacterial infection can be used to induce organotropic protein production.

This problem is solved by a TGC procedure that induces targeted somatic transgenesis, whereby bacteria, carrying a foreign DNA which is integrated into an episomal vector and prepared for subsequent transcription and expression, release their genetic information into an infected single cell when infecting cells, tissue, an organ or the whole host organism and so cause expression of the foreign protein.

This method can be used to obtain a foreign protein but is also advantageous for somatic gene therapy. Here the foreign DNA, introduced into the host organism through bacterial infection, can cause the production of protein missing in the host organism or, by producing single or double strand nucleic acids, can increase, reduce or hinder the production of a protein in the host organism. This method can be used on all known farm animals and also on humans.

If the infected tissue is the egg of a poultry bird, the foreign protein is produced in the egg and can be isolated following known procedures for the isolation of proteins, for example from hen eggs. If the infected tissue is blood cell tissue, the bacteria can spread via parenteral infection of the cells and through them the foreign DNA can reach the entire infected organism. If the host animals are laboratory animals whose infected organ is an udder, the desired foreign protein is then produced in the milk of the laboratory animal from which the foreign protein can then be isolated.

The TGC procedure is discussed below using the *L. monocytogenes* bacterium as an example. It can be similarly used, however, for all bacteria which grow intracellularly, in particular bacteria of the following types: *Aeromonads, Bartonella, Brucella, Campylobacter, Clostridia, Enterobacteriaceae* (in the case of the latter, particularly bacteria of the genus *Yersinia, Escherichia, Shigella, Salmonella*), *Legionella, Mycobacterium, Renibacterium, Rhodococcus* and bacteria from genetically or biochemically related types. Other bacteria types which are non-pathogenic and do not have an intracellular lifestyle are also suited to the method according to the invention, as long as they are viable in a eukaryotic host organism.

It is additionally possible to carry out the TGC procedure with naturally apathogenic bacteria which through genetic manipulation are armed with additional factors which enable their entry into cells. Many naturally occurring bacteria such as *Bacillus subtilis, Lactobacilli, Pseudomonads, Staphylococcus* incapable of intracellular growth can be additionally equipped with a set of pathogenicity factors, for this purpose. One TGC safety strain armed in this way is, for example, *Bacillus subtilis*, which is additionally equipped with listeriolysin from *L. monocytogenes*. An example for the arming of apathogenic bacteria for the TGC safety strain is given in example 1, with the equipping of *L. innocua* with the hly and/or actA gene from *L. monocytogenes*. A further example is *E. coli* K12 armed with the invasin gene (inv) from *Yersinia pseudotuberculosis.*

The TGC procedure is carried out in the following steps:

a) Cloning of the TGC (foreign) DNA:

The TGC method is initiated with the preparation of *L. monocytogenes* strain in the laboratory. The cDNA for the foreign protein to be produced is inserted into a suitable vector. The introduction of the cDNA is carried out in a known way so that subsequent transcription and expression in the eukaryotic host is assured. If the protein is secreted from the cell then the vectors must contain suitable host cell specific secretory signal sequences. The vector can be a eukaryotic vector, for example pCMV from the company Clontech or PCMD from the company Invitrogen, both of which are commercially available. As important criteria for chosen vectors, these have eukaryotic promoters, donors and acceptor sites for RNA splicing (optional property), as well as a polyadenylating site, for example from SV40. The production of genetic constructs (hereafter referred to as TGC DNA below) in *E. coli*, or any other suitable host strain according to the method, can be carried out for the propagation of the DNA. The TGC DNA must simply be able to be introduced into the selected bacteria for the primary cloning and then later transferred into the selected bacterial TGC safety strain. The transfer into *L. monocytogenes* can be carried out using the various well-known methods of gene transfer of isolated DNA (transformation, electroporation etc.) or can be undertaken using the processes of conjugation and transduction either directly or indirectly from bacterium to bacterium.

b) TGC safety strains as recipients of TGC DNA:

Special *L. monocytogenes* host strains are used as recipients of the TGC DNA,—or other TGC hosts, which like *L. monocytogenes* are intracellularly active bacteria (e.g. *Yersinia*) or bacteria which enter the endosome (e.g. *Salmonella*) or are "armed" with additional bacterial factors, or alternatively, otherwise non-pathogenic bacteria (e.g. *Escherichia coli* or *L. innoca*). In all these cases the following properties, singly or in combination, must be met:

(A.1) they are suitable as recipients of foreign DNA (genetic manipulability);

(B.1) they carry mutations which affect genes, without which survival of the bacteria in the environment (outside the host) is not possible, for example, at low ambient temperatures (safety related property);

(B.2) they are attenuated host strains, for which a part of their virulence factors are deleted or inactivated so that they no longer possess the full pathogenicity of the wild-type strains (attenuation);

(C.1) they are "genetically disabled" and can only be cultivated on defined artificial media due to targeted metabolic defects introduced by the experimenter. As a result of these defects they are incapable of growth in a cell and in particular in the animal host and thus cannot proliferate and undergo "endogenous suicide";

(C.2) they induce their uptake in endosomes and are dissoluted in these cell compartments (infection via endosomes);

(C.3) they are ingested by professional phagocytes but can dissolve these cell compartments (i.e. egress) (infection through phagolysosomes);

(C.4) the bacteria carry suicide genes which are only conditionally activated after invading the host cell, so the bacteria kill themselves ("exogenous suicide");

(D.1) they can be eliminated by antibiotic treatment of the intended animal host (killing off through antibiosis).

Point A.1 is a general property of bacteria, without which none of the genetic manipulation mentioned would be possible.

Points B.1 and B.2 summarize alterations which make the use of the bacteria safer. Bacteria with these alterations cannot proliferate if released to the outside world, are attenuated (B.1), or show reduced pathogenic potential (B.2). The alteration of bacteria according to point B.1 has an influence on the release of foreign DNA into the cell (see points C.2 and C.3).

Points C.1-C.4 refer to genetic alterations of bacteria which decisively determine the release of the foreign DNA into the animal cell. In points C.3-C.4 are indicated ways of infection which for bacteria, further summarized below in the examples, were identified as a means for the transmission of foreign DNA into the cytosol of animal cells.

Antibiotic treatment carried out in point (D.1) permits the targeted destruction of bacteria. As a result of this, foreign DNA is released from the bacteria and therapy with antibiotics is also a safety relevant feature.

The alterations and interventions of C.1-C.4 and also B.2 and D.1 enable the release of recombinant DNA into the cell.

Strains with these properties (singly or in combination) are called TGC safety strains.

c) Optimization of the TGC hostss to the target organ of the TGC procedure:

The TGC DNA which codes for the foreign protein to be produced is transferred into the TGC safety strain by transformation, conjugation or transduction. The strains thus obtained are subsequently referred to as TGC hosts. The TGC host strain supplies (feeds) the TGC host organism with DNA and thereby induces somatic transgenesis. In order for the desired foreign protein to be optimally expressed during the TGC process, the gene should be preferably controlled by promoters and other regulatory sequences that either originate from the preselected target organ of the TGC process or are optimized for the target organ, as for example with udder specific promoters and secretion signals.

d) Infection of the host organism with the TGC host:

The propagation of the TGC host by cultivating in vitro in a culture medium is used to prepare it for carrying out the TGC process in the selected host organism. The TGC host strain can alternatively also be propagated in the host organism (human or animal, denoted as TGC host), by in vivo cultivation. In preparation for infection, the TGC host strain is suspended in a non-bactericidal solution adapted for the TGC host, in a buffer or in another physiological liquid. The liquid is administered to the TGC host, for example to the lactating mammal if the udder is to be made somatically transgenic. This can be carried out perorally by drinking the liquid or by supplying it via a stomach tube, the anus or another body orifice. The administration of the TGC host strain by injection is an alternative possibility and can be done intravenously, intramuscularly directly into the target organ or, preferably, intraperitoneally. A further alternative is infecting by producing an aerosol and then inhaling the droplets.

The TGC host (human or farm animal: cow, horse, goat, sheep, pig, hare, poultry etc.) can be infected several times with the same or heterologous transgenes. By repeated infection with different DNA which, for example, code for several enzymes of a biosynthetic pathway, whole enzyme cascades can be established in the TGC host. The biochemical expression of multigenic proteins can thus also be achieved.

e) Organ and cell specificity of infection:

The subsequent path of the TGC host strain in the organism is determined by the natural route of infection. The TGC host strain reaches the target organ using the route typical for the respective bacterium. If the TGC host strain carries genetically unaltered internalin, as in the case of *L. monocytogenes*, then the udder will be among the target organs. Genetically altered internalins permit the infection of other organ systems. Depending on its infection cycle, the TGC host strain penetrates into the cells and appears in the cytoplasm. As it is genetically defective, the TGC host strain cannot proliferate there and it undergoes "endogenous suicide" (see C.1 under b) above). With cell infection the TGC host strain has introduced the host-foreign TGC DNA into the cell. The transfer of foreign DNA into the cell can, however, also be brought about by "exogenous suicide" (see C.4 under point b) above) or by elimination the bacteria through specific antibiotic treatment (see C.3 under point b) above). In these three cases the bacteria cells carrying the foreign DNA die within the animal cells and thereby release the foreign DNA into the cytoplasm. Finally, the transfer of the foreign DNA into animal cells can also be achieved by targeted infection of cells with absence of lysis of the endosomes. The foreign DNA of the animal cells is thus available within the endosomes by lysis of the bacteria.

In each of the cases mentioned, the DNA transferred into the cells is now available as a template for the production of the desired foreign protein. The nucleic acid can also have a direct therapeutic effect however, for example by the generation of anti-sense RNA. The cells, tissue or organ manipulated in this way became somatically transgenic in the course of the infection.

f) *L. monocytogenes* induced protein production in the milk of mammals

After carrying out the TGC procedure—for example with TGC host strain such as *L. monocytogenes* or other intracellularly active bacteria (e.g. *Yersinia*) or bacteria which penetrate the endosome (e.g. *Salmonella*) or are "armed" with additional bacterial factors, or otherwise non-pathogenic bacteria (e.g. *Escherichia coli* or *L. innocua*)—the protein is created in the lactating cell and passed out into the milk with the other products of the cell. If several animals are made somatically transgenic with different foreign DNA in a TGC process, then the different proteins can be produced, separated from each other, by collecting the milk of each single TGC host (milking).

Due to the properties of the TGC host strain, no *L. monocytogenes* (TGC host strain, i.e. host bacterium) appear in the milk. Should this be the case however, then the bacteria can be eliminated using the methods familiar to an expert in the field, for example by treating with antibiotics. Animals (or also humans) are free of any viable, genetically engineered organisms after carrying out targeted genetic conditioning (TGC) and do not therefore have to submit to any further safety checks. The TGC host transmits the genetic information introduced into it by the TGC process to the offspring cells in the context of usual cell division. The information is not transmitted to the descendants of the TGC host however, as the TGC DNA is not present in the germ line of the TGC host. The avoidance (i.e. omission) of genetic manipulation of the germ line of the whole organism and targeted protein production in a predetermined organ or tissue of the animal host (animal and human) constitutes the innovative and new aspect of the method according to the invention.

g) Infections of tissue by *L. monocytogenes*

Blood is a tissue whose genetic alteration using the TGC method according to the invention will be described as an example. Blood cells are particularly suited for the TGC method. It is possible to infect blood cells outside the body. The desired somatic transgenesis of the cells can similarly be monitored outside the host. In the case of attenuated auxotrophic bacteria—diaminopimelic acid is here used as an example for auxotrophy—the substances necessary for the growth of the cells can be added to the medium and thus control the life span of the bacteria according to the experimental objective. It is possible to check whether the intracellular bacteria are still alive by subsequent lysis of the animal cells.

The transfected cells, containing a well defined quantity of live bacteria, are finally used for reimplanting in the recipient organism. In particular cases there can be such a large number of bacteria that additional organs in the organism are infected. In other cases transgenesis is specifically restricted to the blood tissue by the in vitro elimination of live bacteria before reimplantation in the TGC host.

Reimplantation and the connected dissemination of transgenic cells with or without live bacteria permits somatic gene therapy of cells in the host, which in this case may also be a human host.

The TGC method also enables extracorporal proteins to be produced. For this purpose TGC host strains are injected into the eggs of poultry birds. Suitable techniques for this are state of the art in the production of vaccines by viral agents. During the incubation period the cells in the egg are infected in a somatic transgenic process and then produce the foreign protein. The foreign protein can be purified from the egg using state of the art techniques. With this type of TGC process the TGC host strain remains controllable in all stages of use under laboratory conditions. The quantity of protein to be produced depends only on the injection of a correspondingly large number of eggs.

h) Use of the TGC method for somatic gene therapy

There is not yet an established form of somatic gene therapy. At present the nucleic acid used for transfection is protected from the influence of the outside world within viruses or packed in liposomes.

Viruses have the disadvantage that they only have a limited size uptakecapacity and that the development of their full cytopathic effect at high infection doses must be taken into account [32a]. They induce immune reactions and so can be attacked and destroyed themselves. Some viruses are inactivated by serum and are then unusable for gene therapy. Here particularly, mention should be made of the multiple dosage of viruses for gene therapy, in the course of which the immune response of the host is stimulated. The creation of a specific defense aimed against viruses has proved to be a significant problem in the use of viruses in the context of gene therapy.

When using liposomes, the toxic effect of lipids in provoking inflammatory reactions must be considered.

In the case of in vivo therapy there are still considerable obstacles to using the gene transfer systems used so far. For this form of therapy it is necessary to have [32b]:

(i) Resistance of the vector against breakdown after in vivo administration in the body,
(ii) Tissue specificity, i.e. targeted control of the tissue (organ) being subjected to therapy and
(iii) Safety, by which is meant harmlessness to organs not being treated [32b].

The bacteria described in this patent application, which function as a vehicle for gene delivery are ideally suited for gene transfer. The bacteria are optimally adapted to their corresponding host and can survive in it for a sufficient length of time without external intervention, such as antibiotic therapy. They induce specific diseases following a defined route of infection and in so doing partly display marked organotropy. They can take up considerable quantities of foreign DNA (e.g. naturally occurring plasmids have sizes of several hundred kilobases), so not only cDNA's but even larger regions of a chromosome can be transferred. Finally, they can be used safely, particularly if "disabled" bacteria are used, as described above. The genetic defects of the TGC host strain, in combination with their antibiotic sensitivity, assure efficient elimination of the bacteria after they have completed their task of DNA transfer into eukaryotic cells.

EXAMPLE

Examples for somatic gene therapy are listed below:

Therapy for cystic fibrosis (CF): the bacterium must here be administered by inhalation to the patient undergoing therapy. The bacterium used should preferably be a bacterium which is transmitted through droplet infection. The bacterium contains the CFTR gene, which can cure the crucial defect occurring in CF. The bacterium penetrates into the airway lumen-facing columnar cells and transfects them with the CFTR DNA integrated into the TGC vector. The cells become somatically transgenic, the defect is cured.

β-thalassaemia can be treated by somatic gene therapy with human β-globulin gene. Ex vivo cells that originate from the haemopoetic system are infected with a TGC safety strain, which transfers the β-globulin gene into the original cell. The infecting bacterium is eliminated by treatment of the cells in the cell culture and the transgenic cell is prepared for transfer back into the human. This transfer takes place through intravenous administration.

In therapy of Hurler syndrome, naive CD34 positive cells of the bone marrow are transfected with α-L-iduronidase gene. The way gene therapy is carried out and the transfer of the cells back into the patient are as described in the preceding example.

In gene therapy of *Fanconi anaemia*, the gene of the *Fanconi anaemia* complementation group C (FACC) is used for somatic gene therapy. The target cells of the infection with TGC host strain are again CD34 positive cells of the bone marrow.

i) Proof of the Success of TGC Method

DNA transfer is already evident in mice within the first 24 hours, i.e. long before a specific immune response against the bacterium could arise. This was demonstrated by the production of β-galactosidase or the green fluorescent protein (EGFP) in cell cultures within 24 hours. The "mitogenetic effect of bacteria", which additionally occurs in the context of infection, favours the establishment of DNA in the TGC cell and is therefore desired and advantageous for the success of the TGC process.

In summary, it can be established that the use of bacteria for somatic gene therapy is safer than gene therapy using viral systems. Bacterial infection can both be directed and restricted locally. Growth and hence florid infection by the bacteria can be prevented by removing particular bacterial factors. Additionally the growth of bacteria in eukaryotic cells can be directly influenced and generally prevented. Finally, the termination of bacterial infection is possible at any time through the use of antibiotics, i.e. the place, time and effectiveness of the infection can be controlled.

The invention is described in detail below, using *L. monocytogenes* as an example:

Example 1

Production of TGC Safety Strains

The *L. monocytogenes* safety strains are produced by targeted genetic alterations of primary pathogenic *L. monocytogenes*. In so doing, several levels of safety are established together. Recurrence of vitality or pathogenicity caused by reversion of the mutations is prevented. The mutations affect genes which (1) influence the survival of bacteria in the cell, (2) which diminish the pathogenicity of the bacteria in the TGC host and (3) which prevent survival of the bacteria in the environment, should any escape.

a) First level of safety—safety relevant property: survival in the environment (see point B.1 under b) above)

TGC host strain s can be applied to the TGC host either by injection or by peroral administration. With peroral administration there may be a surplus of bacteria, resulting in secretion of bacteria, which are not ingested by the organism. In order that these eliminated bacteria have no opportunity of surviving in the environment, the TGC safety strain can contain additional mutations which prevent the growth of the bacteria in the environment.

As an example for this, the switching off of the cspL gene (cold shock protein of Listeria) is indicated. This has the consequence that the bacteria can no longer grow at temperatures under 20° C. Growth and ability to infect at 37° C. are not adversely affected, but are additionally modulated by simultaneous mutations according to a) and b). The cspL gene, which is deleted in the safety strains used in this invention, is shown in the sequence protocol under SEQ. ID No. 2. A corresponding cspL deleted strain identified by accession number DSM 11883 with the description *L. monocytogenes* EGD delta cspL1 was deposited on Dec. 9, 1997 at the German Depositor Authority DSM, "Deutsche Sammlung von Mikroorganismen und Zellkulturen GmbH" at Mascheroder Weg lb, D-38124 Braunschweig, under the Budapest Treaty on the International Recognition of the Deposit of Microorganisms for the Purposes of Patent Procedure.

The TGC safety strains of the invention can only be cultivated on special growth substrates. The growth temperature must be above 37° C., growth is not possible below 20° C. The bacteria possess limited pathogenicity and are only capable of penetrating restricted, tightly defined areas of the TGC host. In this way safety of the system for humans and the environment is assured. The TGC host strains are no longer able to grow outside the artificial media, here specifically, the host cell. This restricted intracellular viability is at the same time a prerequisite for the release of TGC DNA in the host cell and hence for the induction of somatic transgenesis using the TGC method.

b) Second level of safety—attenuation: reduced pathogenicity (see point B.2 under b) above)

The second level, of attenuation of the TGC safety strains includes mutations in the pathogenicity factors. Through targeted mutations in defined factors, pathogenicity in the bacteria is reduced, induced apoptosis of infected host cells is prevented and the immune reaction is at the same time directed in the desired direction. The mutations restrict the intracellular motility of the bacteria and hence their spread to secondary cells. The infection is thus limited to the chosen target cells, with retention of treatment using antibiotics.

For safety considerations it is desirable to restrict or even prevent the intracellular spread of the TGC host strain after infection. Accurate knowledge of the intracellular lifestyle and the motility of the above mentioned bacteria makes it possible to produce defined, stable mutants with reduced ability to infect the TGC host organism.

With *L. monocytogenes*, the mutations attenuated in this way affect, for example, the hly gene with consequent blocking of infection in the first cell. An example for the switching off of this pathogenicity factor, the strain described as *L. monocytogenes* EGD HIY.sub.D491A and having the accession number DSM 11881 was deposited on Dec. 9, 1997 at the German Depository Authority DSM, "Deutsche Sammlung von Mikroorganismen und Zellkulturen GmbH" at Mascheroder Weg lb, D-38124 Braunschweig, under the Budapest Treaty on the International Recognition of the Deposit of Microorganisms for the Purposes of Patent Procedure.

Another example for the reduction of pathogenicity of *L. monocytogenes* are mutations in actA gene or the deletion of regions which are necessary for the interaction between actA and the host cell protein VASP, with the consequent blocking of intracellular motility. Finally, there are mutations of plcB gene, in which bacteria are disabled for spread into a second cell. The deposited strain *L. monocytogenes* EGD delta actA delta plcB is an example of a double mutation in which both the actA gene and the plcB gene are removed. This strain, identified by the accession number DSM 11882 and having the description of *L. monocytogenes* EGD delta actA delta plcB, was deposited on Dec. 9, 1997 at the German Depository Authority DSM, "Deutsche Sammlung von Mikroorganismen und Zellkulturen GmbH" at Mascheroder Weg lb, D-38124 Braunschweig, under the Budapest Treaty on the International Recognition of the Deposit of Microorganisms for the Purposes of Patent Procedure.

It is additionally possible to exchange the wild-type listeriolysin gene in *L. monocytogenes* for a mutated allele. The properties of the listeriolysin are then restricted, both for inducting apoptosis in various host cells and also for generating a strong T cell mediated immune response.

C) Survival in the cell: —endogenous suicide: third level of safety (see point C.1 under b) above)

In general one of the features of attenuated bacteria for the TGC process is their having defined deletions in the genes which are essential for the biosynthesis of integral bacterial components. The selected auxotrophic bacteria are suitable as TGC host strains, since, being attenuated bacteria, they can transport foreign DNA into the cell. However, as the bacteria in the cells lack essential "growth factors", they spontaneously lyse and thereby release TGC DNA in the cell.

*L. monocytogenes* are used as TGC safety strains. They are genetically altered in such a way that although they infect the cell, they can no longer multiply in the cell. This is achieved by, for example, inactivating the dapE gene in *L. monocytogenes*. *Listeria* are gram positive bacteria which, just like gram negative bacteria, require meso-diaminopimelic acid derivative (DAP) for cross-linking of the cell wall. Biosynthesis of diaminopimelic acid is therefore essential for the creation of the bacterial cell wall. DAP auxotrophic bacteria succumb to spontaneous lysis if this amino acid is no longer supplied in the culture medium. The enzymes which are involved in DAP synthesis in bacteria are not present in mammalian cells. In TGC safety bacterial strains, these enzymes are also deleted or inactivated by insertions or other means. The dapE of *L. monocytogenes*, which was inactivated in the safety strains used according to the invention, is shown in the sequence protocol as SEQ. ID No. 1. For the genetic manipulation of the dapE gene in *L. monocytogenes*, its sequence had to be determined, as corresponding genes, e.g. from *E. coli*, has only about 30% homology to the sequence of SEQ ID No. 1 protocol.

The bacteria deleted for this or other genes of the DAP biosynthesis pathway, so called DAP mutants, cannot grow either within or outside the host. In order to grow they require the addition of a large quantity of DAP (1 mM) to the growth medium. If DAP is missing, the bacterium cannot survive either in the TGC host or outside the TGC host. These DAP mutants hence provide safety, both against a bacterial infection of the TGC host and safety against an infection of other organisms in case of release of a strain of this type into the environment.

A manipulation of the genome of *Salmonella* (creation of an auxotrophic mutant) shows that the deletion (or blocking or mutagenesis) of the aroA gene, which is essential for the synthesis of aromatic amino acids, has the same effect. From the *Salmonella* vaccine strain (available from the American collection of bacterial strains under the number ATCC14028), a mutant can be produced by genetic manipulation using techniques well-known to experts, and with knowledge of the aroA gene sequence (Genebank accession number M10947). This mutant can function as a TGC safety strain in a similar way to the recombinant bacteria here described for Listeria. Release of foreign DNA occurs, as for the above described *L. monocytogenes* delta dapE strain, through the bacteria dying off after their uptake into the cell. Unlike *L. monocytogenes, Salmonella* cannot enter the cell cytoplasm. Release of the foreign DNA in this case occurs from the endosomes into the cell cytosol.

Other attenuated mutations of *L. monocytogenes* are also known, in which biosynthesis of nucleic acids, amino acids, sugars or other essential cell wall ingredients, is blocked [33 to 35]. The same can also be achieved through mutations in regulatory genes which are essential for the intracellular lifestyle of the bacteria. An example of a gene of this type is phoP of *Salmonella typhimurium* [36].

The examples described here for *L. monocytogenes* can be applied to other intracellular live bacteria or bacteria which are first made into intracellular activators by being armed with pathogenicity factors. This is especially the case for bacteria of the types *Aeromonads, Bartonella, Brucella, Campylobacter, Clostridia, Enterobacteriaceae* (particularly *E. coli, Salmonella, Shigella, Yersinia*), *Mycobacterium, Renibacterium* and *Rhodococcus*. A TGC safety strain accordingly armed, for example, *Bacillus subtilis*, which is additionally equipped with listeriolysin from *L. monocytogenes*.

An important prerequisite for transfer of DNA itself into cells distal in the body is the protection of the DNA on its way to the target cell or target tissue or target organ. The ability of intracellular live bacteria such as *L. monocytogenes* to spread intracellularly is an ideal property for transporting genes into isolated cells, deeper tissue and organs. The vehicle, the TGC host strain, dies after successful transfer of TGC DNA into the target cell, as a consequence of attenuation (B.1), induction of auxotrophy (B.2), endogenous suicide (C.1), infection by endosomes (C.2), infection by phagolysosomes (C.3), exogenous suicide (C.4) or antibiotic therapy (D.1).

Example 2

Release of Foreign DNA in Animal Cells (Tissue or Organ)

A) Infection via endosomes: Transfer of the expression plasmid without release of the bacteria from the endosome vesicle (see point C.2 under b) above)

Tests were carried out to see if bacteria are able to transfer their plasmid DNA into the cytoplasm of infected host cells, without it being necessary for them to first escape from the endosome vesicle. The ability of *L. monocytogenes* Δhly mutants, which can no longer leave the endosome, to function as a transfer bacterium for DNA transfer was investigated. EGFP was chosen as the foreign DNA to be transferred. It is a fluorescent protein which was cloned under the control of a CMV promoter. As a measure for successful transfer of foreign DNA—i.e. as a measure for transfection of the eukaryotic cells—10,000 cells were examined in a FACS scanner for the occurrence of EGFP dependent fluorescence, after infection with the corresponding *L. monocytogenes* strains. The number is expressed in Table 1 as a percentage of the total number of measured eukaryotic cells. *L. monocytogenes* wild-type strain EGD served as a positive control during the experiments. An isogenic non-invasive ΔInlAB strain was also tested. The evidence obtained with these bacteria have general validity and are transferable to other bacteria.

The results are summarized in Table 1 and show that Δhly mutant is just as efficient as the wild-type *L. monocytogenes* strain with regard to DNA transfer from the bacterium into the eukaryotic cell. The *L. monocytogenes* ΔInlAB strain is not suitable (PtK2) or is significantly worse (Hep-2) as a vehicle for DNA transfer into the cells here indicated. The experiments also show that the active uptake of bacteria by eukaryotic cells (in this case non-professional phagocytes) is a precondition for transfection of cells. The attachment of bacteria is effected by the interaction between bacterial internalins (InlA and/ or InlB) and the receptors of the animal cells. The experiments of the following example demonstrate that inter nalin is not necessary for the uptake of bacteria in professional phagocytes.

| Cell line | Origin | L. monocytogenes strain | Transfected cells in % |
|---|---|---|---|
| PtK2 | Kangaroo rat kidney | Wild-type EGHD | 1.71 |
| | | Δhly | 1.78 |
| | | ΔinlAB | 0 |
| Hep-2 | Human larynx carcinoma | Wild-type EGHD | 4.58 |
| | | Δhly | 4.31 |
| | | ΔinlAB | 0.24 | b) Infection through phagolysosomes: Arming of non-pathogenic strains as TGC safety strain; (see point C.3 under b) above)

The example shown below for *L. innocua* is representative and can be extended to other non-pathogenic bacteria (e.g. *Escherichia coli*). The steps leading to the genetic manipulation of such bacteria correspond to those here indicated for *L. innocua*.

A non-pathogenic *L. innocua* strain (Serovar 6a) was "armed" with the pathogenicity factors listeriolysin and ActA from listeria monocytogenes. In order to be able to regulate this gene, the positive-regulatory factor (PrfA) was cloned as third gene into genetically engineered *L. innocua* strain. The presence of PrfA causes expression of the virulence gene to be growth temperature dependent. As this recombinant *L. innocua* strain possesses no internalin, i.e. is not itself invasive, it cannot penetrate into the above mentioned cells (Ptk2, Hep-2). If the experimenter wishes to be able to also infect these cells, then the bacteria must additionally be equipped with the internalins InlA and/ or InlB. The experiments of the present example show that there is no need of these bacterial products (internalins) for the ingestion of *L. innocua* (hly+; actA+) strain by professional phagocytes. After their phagocytosis, the *L. innocua* strain (hly+; actA+) uses the protein listeriolysin for the lysis of the phagolysosomes of the professional phagocytes. It can be seen from the electron micrographs that the genetically manipulated *L. innocua* (hly+; actA+) strain appears in the cytoplasm of the professional phagocytes. The wild-type strain *L. innocua* Serovar 6a, on the other hand, is killed off in the phagolysosome and does not appear in the cell cytoplasm. Expression of the ActA-protein enables the *L. innocua* (hly+; actA+) strain to have an actin cytoskeletal-dependent intracellular movement, which appears similar to the movement of the *L. monocytogenes* strains in the EM images. Due to the failure of further genes, such as e.g. the plcB gene, the *L. innocua* (hly+; actA+) strain mentioned here cannot spread to neighbouring cells. This specific alteration in infectivity has already been described for recombinant *L. monocytogenes* ΔplcB strains.

The targeted selection of genes, here hly and actA, and their transformation into non-pathogenic bacteria, transfers the selected *L. monocytogenes* properties to non-pathogenic bacteria. The escape of the bacteria from the "deadly" phagolysosome is a precondition for the transfer of foreign DNA into infected cells. The DNA which is to be transferred for the reprogramming of animal cells, is thereby integrated into host strains, as described above for attenuated *L. monocytogenes* bacteria—which according to the invention can be used as such. The release of the genetic information according to the invention occurs through (i) creation of auxogenous mutants (deletion of endogenous, life-essential genes), (ii) through introduction of "suicide genes", (iii) through induced ingestion into endosomes and killing off there or (iv) through antibiotic therapy which is temporally defined and directed to killing bacteria in a target organ or tissue.

The experiments of this example are representative of how naturally occurring non-pathogenic bacteria can be consecutively "armed". By equipping them with defined bacterial factors (here genetic i.e. properties of naturally invasive bacteria), bacteria which are otherwise primarily unsuited for the TGC method can be manipulated and directed in such a way by the experimenter so that they can be used for controlled infection and transfer of DNA into animal cells (or tissue, organ, whole animal, human).

c) Release through exogenous suicide: Cloning of suicide genes: (see point C.4 under (b) above)

Suicide genes, which are activated after penetrating into the host cell and lead to death of the bacteria, can be supplied to the bacteria in the form of lysis genes from bacteriophages, for example with the S-gene of the lamda or analogous bacteriophages [37], or with killer genes from plasmids [38]. These genes are controlled by an intracellular inducable promoter (for example pagC-promoter from *Salmonella [*38]).

d) Release through antibiotic therapy: Targeted release of foreign DNA in the lung after droplet inhalation of *Listeria monocytogenes* (see point D.1 under (b) above).

Infection with bacteria took place according to the method "Body plethysmography in spontaneously breathing mice" by R. Vijayaraghavan [Arch. Toxicol. 67: 478-490 (1993)]. In the experiment mice were exposed singly for half an hour in an inhalation chamber to an aerosol of one millilitre of bacterial suspension, which contained a total of 5000 bacteria. This quantity of bacteria corresponds to the LD50 dose of intraperitoneally administered bacteria. In order to be able to follow the course of the infection in real time, the bacteria were once more transformed with a EGFP-gene construct. Using fluorescence analysis of the EGFP-protein formed in the tissue, the route of infection of the bacteria in the animal model was followed. Within half an hour the bacteria penetrate into the columnar and endothelial cells of the air passage. At this point no bacteria are to be found in other tissue or organs of the infected animal, such as e.g. spleen, liver, brain. The infection remains exclusively restricted to the lung for up to 18 hours. Only after 24 hours are other organs also affected.

The experiment shows that the spread of bacteria after droplet infection can be restricted to the primary organ if there is an intervention into their viability. Two ways of achieving this are by using attenuated mutants (e.g. ActA deleted in the "spreading gene") and/or by destroying the bacteria through initiating antibiotic therapy at a time determined by the experimenter, i.e. in an organ determined by the experimenter.

Example 3

Description of the TGC Vectors

TGC vectors are episomal DNA, for example plasmids with low ingestion capability for foreign DNA (pMB derivatives which are sufficient for single genes), or plasmids with greater DNA ingestion capability (such as in Pl- or F-plasmids), in order to create somatic transgenesis for complex biosynthetic pathways.

In all cases, the plasmids involved are replicated in the bacteria hosts which are used for genetic alteration and cultivation for the TGC process. *E. coli*, or other bacteria commonly used in recombinant DNA techniques, are suited as examples of an intermediate host in which genetic building blocks can be constructed. *L. monocytogenes* or other above-mentioned bacteria functioning as TGC host strainss are suitable as a TGC safety strain. In order to fulfil this condition, the plasmids contain the host-specific plasmid replicon sequences. During the process of generating recombinant DNA, the transformed host cells must be distinguished from "naked" host cells. Generally, common antibiotic resistance genes can be used as selection principles for this.

Example 4

Transformation of L. monocytogenes Safety Strains to TGC Host Strains

The transformation of L. monocytogenes is carried out according to a modified protocol of Park and Stewart [40].

Accordingly, bacteria are applied up to an optical density of $OD_{600}$=0.2. Ampicillin (10 µg/ml) and 1 mM glycine are added to the culture medium. Further proliferation occurs up to an $OD_{600}$ of 0.8 to 1.0. The cells are harvested by centrifugation and resuspended in 1/250 vol. cold electroporation buffer (1 mM Hepes, pH 7.10, 0.5 M sucrose). The bacteria are washed up to four times prior to electroporation.

For electroporation, 50 µl of the prepared cells are added to an electroporation cuvette, electroporation is carried out using 1 µg DNA at 10 kV/cm, 400 ohms, 25 µF.

After electroporation the cells are immediately cooled on ice, suspended in 10× BHI medium and incubated for 2 hours at 37° C. with careful agitation. After this the cells are plated and incubated at the desired temperature. The efficiency of transformation with this method is $10^4$ to $10^5$ transformers per µg plasmid DNA used.

Example 5

Description of the Cultivation of TGC Host Strains For Use in the TGC Method

Listeria were preferably cultivated in the brain-heart infusion broth, for example BHI of the Difco company. Alternatively, and for special applications (radioactive labelling of listerial proteins), the bacteria can be cultivated in tryptic soy broth (TSB) or in Listeria minimal medium (LMM) [36]. The bacteria are centrifuged off and washed several times in a suitable transfer medium, for example, a bicarbonate containing buffer.

Bacteria prepared in this way can be kept for at least 6 months at −80° C. with the addition of 15% glycerine solution, before they are used in the TGC procedure.

Example 6

TGC Method—Use of TGC Host Strains as Nutrient

As an introduction to the TGC process, the animals are not allowed to drink for a few hours. The (TGC host strain: TGC-DNA in the desired strain) are infused in a bicarbonate containing buffer of suitable concentration and administered to the animals orally, by inhalation or by injection (parenteral, intramuscular, intraperitoneal or directly into the target organ). The type of application is determined by the physiological route of infection of the corresponding TGC hot strain. The selection of the bacterium which is used as TGC safety strain depends on the target organ and is established according to the path of infection and according to the organotropy of the relevant bacterium. The dosage of bacteria is chosen so as to achieve the desired organotropic transfection of the TGC host strain. The quantity and type of bacterial application thus depends on the particular bacterium, but also depends on the host and target organ (see also example 2).

Example 7

Implementation of Somatic Gene Therapy

Examples for somatic gene therapy are listed below:

Therapy for cystic fibrosis (CF): the bacterium must be administered by inhalation to the patient undergoing therapy. The host used should preferably be a bacterium which is transmitted through droplet infection. The bacterium contains the CFTR gene, which can cure the crucial defect occurring in CF. The bacterium penetrates into the airway lumen-facing columnar cells and transfects them with the CFTR DNA integrated into the TGC vector. The cells become somatically transgenic, the defect is cured.

β-thalassaemia can be treated by somatic gene therapy with human β-globulin gene. Ex vivo haematopoetic stem cells are infected with a TGC safety strain, which transfers the β-globulin gene into the original cell. The infecting bacterium is eliminated by treatment of the bacteria in the cell culture and the transgenic cell is prepared for transfer back into the human. This transfer takes place through intravenous administration.

In therapy of Hurler syndrome, primitive CD34 positive cells of the bone marrow are transfected with α-L-iduronidase gene. The way gene therapy is carried out and the transfer of the cells back into the patient are as described in the preceding example.

In gene therapy of Fanconi anaemia, the gene of the Fanconi anaemia complementation group C (FACC) is used for somatic gene therapy. The target cells of the infection with TGC host strain are again CD34 positive cells of the bone marrow.

Example 8

Monitoring the Success of Induced Somatic Transgenesis

After the TGC DNA has been transferred into the TGC host, the success of the TGC process has to be monitored. Immunological methods for detecting gene products (proteins) are suited for this, such as immunoassays (e.g. ELISA), immunoblot or other well-known methods which involve an antigen-antibody reaction. T-cell responses can be measured in special assays and are always used when the antigen is a substance that is recognized via MHC-class 1 mediated immune responses.

If the protein produced is an enzyme, then its biological activity can be determined in the form of an enzyme activity test. If the protein additionally possesses biological activity, then the efficiency of the protein produced can be measured with biological assays.

For proteins that induce passive or active immunisation of the TGC host, protection against the activating agent can be tested; for example, the prevention of colonisation, infection (or apparent disease) in the experimental animal after exposure to the pathogenic organism (bacterium or virus).

Example 9

Harvesting the Protein

The protein to be produced can be obtained using state of the art techniques that are common knowledge to persons involved in animal husbandry:

- if the TGC host is a cow or other lactating farm animal and the udder is the infected organ, then the well-known techniques of milking can be used;
- if poultry birds such as hens were used as the TGC host, then the eggs are collected and taken to the protein purification stage;
- processing of proteins from organs whose products cannot be externally accessed is achieved by obtaining the relevant organs, for which the animal must usually be killed, e.g. with fish;
- if the somatic transgenic tissue is blood, then the desired product is obtained after venous aspiration, from the blood or its cells and purified by methods familiar to the expert.

Example 10

Initial Purification of the Protein

Preliminary purification of the protein to be produced is achieved by separation processes, which are familiar to the expert as mainly physical or physico-chemical methods. Amongst these are precipitating the proteins using salts (for example, ammonium sulphate), acids (for example, trichloroacetic acid) and using heat or cold.

A rough separation can also be achieved via column chromatography. All the methods used here strongly depend on the primary media in which the protein is enriched. For example, many methods are known for the processing of milk or eggs in industry, and they can be used in the invention described here. The same also applies to processing of blood as a somatic transgenic tissue. Here it is possible to refer to the experience of transfusion medicine, particularly the processing and purification of blood clotting factors.

Example 11

Purification of the Protein

For the final purification of the proteins, all the methods used in conventional purification of proteins can be used. Amongst them are:

- purification using affinity chromatography, for example exploiting the receptor-ligand interaction;
- the preparation of fusion proteins with so-called "tags", which can be used for specific interaction with a matrix in chromatography (for example, polyhistidine tag and nickel column chromatography; the streptavidin-biotin technology of affinity purification). The tags can be then removed by appropriate introduction of a corresponding protease cutting site allowing subsequent release of the desired protein following protease digestion;
- purification via specific antibodies (immunoaffinity chromatography);
- the exploitation of natural affinities between the target protein and other proteins, carbohydrates or other binding partners, as in the case of toxin A of Clostridium difficile, which binds to thyroglobin at 4° C. and is subsequently eluted by raising the temperature to 37° C.

Example 12

Production of TGC Proteins

The list of proteins which it is possible to produce with the TGC method is theoretically unlimited and above all includes the range of hormones, regulatory factors, enzymes, enzyme inhibitors and human monoclonal antibodies, as well as the production of surface proteins of pathogenic microorganisms or viral envelope proteins so as to safely produce diagnostic tests and vaccines which can be tolerated. The list covers high volume products such as human serum albumin and also proteins used in smaller quantities, such as hirudin, blood clotting factors, antigens for tumour prophylaxis and for active immunisation (for example, papilloma antigen) or for passive immunisation.

Bibliography

1. Cossart, P. and Finlay, B. B. "Exploitation of mammalian host cell functions by bacterial pathogens". Science 276: 718-725.
2. Falkow, S., Isberg, R. R. and Portnoy D. A. (1992). "The interaction of bacteria with mammalian cells". Ann. Rev. Cell Biol. 8: 333-63.
3. Weinberg, A. N., "Zoonoses", in Principle and Practice of Infectious Diseases. Eds. Mandell, Douglas and Bennett, J. E. and Dolin R., pp. 291-295. Churchill Livingstone, New York, 1995.
4. Farber, J. M. and Peterkin, P. J. (1991). "*Listeria Monocytogenes*—a foodborne pathogen". Microbiol. Rev. 55: 476-511.
5. Thoen, C. O. (1994). "Tuberculosis in wild and domestic animals", in Tuberculosis: Pathogenesis, Protection and Control, pp. 157-62. ASM, Washington D.C. 20005.
6. von Hase, U., Pulz, M., Windorfer, A. "EHEC in Niedersachsen, January 1995-August 1997". Niedersächs. Ärztebl. (1997), pp. 20-23 and 38-40.
7. Swaminathan B., Rocourt J., and Bille J. (1995). "*Listeria*", in Manual of Clinical Microbiology. Eds Murray, P. R., Baron, E. J., Pfaller, M. A., Tenover, F. C., and Yolken, R. H., pp. 341-348. ASM Press, Washington D.C.,
8. Hof, H., Nichterlein, T., and Kretschmer, M. (1997). "Management of Listeriosis". Clin. Microbiol. Rev. 10: 345-357.
8a. Simon, S. and Stille, W., "Antibiotikatherapie". Schattauerverlag.
9. Chakraborty, T. and Wehland, J. (1997). "The host cell infected with *Listeria monocytogenes*", in Host Response to intracellular pathogens, pp. 271-290, Ed. S. H. E. Kaufmann R. G. Landes Co., Austin, USA.
10. Gaillard, J. L., Berche, P., Frehel, C., Gouin, E. and Cossart, P. (1991). "Entry of *L. monocytogenes* is mediated by internalin, a repeat protein reminiscent of surface antigens from gram-positive cocci". Cell, 65: 1127-1141.
11. Lingnau, A., Domann, E., Hudel, M., Bock, M., Nichterlein, T., Wehland, J. and Chakraborty, T. (1995). "Expression of inlA and inlB in *L. monocytogenes* EGD, whose products mediate bacterial entry into tissue culture cell lines, by PrfA-dependent and -independent mechanisms". Infect. Immun., 63: 3896-3903.
12. Alvarez-Dominguez, C., Carasco-Martin, E., and Levya-Cobian, F. (1993). "Role of comolement comopnenet Clq in phagocytosis of *L. monocytogenes* by murine macrophage-like cell lines". Infect. Immun., 61: 3664-3672.
13. Dunne, D. W., Resnick, D., Greenberg, J., Krieger, M., and Joiner, K. A. (1994) "The type I macrophage scavenger receptor binds to Gram-positive bacteria and recognizes lipoteicheoic acid". Proc. Natl. Acad. Sci. USA, 91: 1863-7.

14. Gaillard, J. -L., Berche, P., and Sansonetti, P. J. (1986). "Transposon mutagenesis as a tool to study the role of hemolysin in virulence of *Listeria monocytogenes*". Infect. Immun., 52: 50-55.

15. Theriot, J. A., Rosenblatt, J., Portnoy, D. A., Goldschmidt-Clermont, P. J., and Mitchison, T. J. (1994). "Involvement of profiling in the actin-based motility of *Listeria monocytogenes* in cells and cell-free extracts". Cell 76: 505-517.

16. Chakraborty, T., Ebel, F., Domann, E., Niebuhr, K., Gerstel, B., Pistor, S., Temm-Grove, C. J., Jockush, B. M., Reinhard, M., Walter, U., and Wehland, J. (1995). "A focal adhesion factor directly linking intracellularly motile *Listeria monocytogenes* and *Listeria ivanovii* to the actin-based cytoskelton of mammalian cells". EMBO J. 14: 1314-21.

17. Vazquez-Boland, J. A., Kocks, C., Dramsi, S., Ohayon, H., Goeffroy, C., Mengaud, J., and Cossart, P. (1992). "Nucleotide sequence of the lecithinase operon of *L. monocytogenes* and possible role of lecithinase in cell-to-cell spread". Infect. Immun. 60: 219-30.

18. L'Hopital, S. J., Marly, J., Pardon, P., and Berche, P. (1993). "Kinetics of antibody production against listeriolysin O in sheep with listeriosis". J. Clin. Microbiol. 31: 1537-40.

19. Domann, E., Zechel, S., Lingnau, A., Hain, T., Darji, A., Nichterlein, T., Wehland, J., and Chakraborty, T. (1997). "Identification and characterization of a novel PrfA-regulated gene in *listeria monocytogenes* whose product, IrpA, is highly homologous to internalin proteins, which contain leucine-rich repeats". Infect. Immun. 65: 101-9.

20. Grenningloh, R., Darji, A., Wehland, J., Chakraborty, T., and Weiss, S. (1997). "Listeriolysin and IrpA are major protein target of the human humoral response against *Listeria monocytogenes*". Infect. Immun. 65: 3976-3980, 1997.

21. Shen, H., Slifka, M. K., Matloubian, M., Jensen, E. R., Ahmed, R., and Miller, J. F. (1995). "Recombinant *Listeria monocytogenes* as a live vaccine vehicle for the induction of protective anti-viral cell-mediated immunity". Proc. Natl. Acad. Sci. USA 92: 3987-91.

22. Slifka, M. K., Shen, H., Matloubian, M., Jensen, E. R., Miller, J. F. and Ahmed, R. (1996). "Antiviral cytoxic T-cell memory by vaccination with recombinant *Listeria monocytogenes*". J. Virology 70: 2902-10.

23. Jensen, E. R., Selvakumar, R., Shen, H., Ahmed, R., Wettstein, F. O., and Miller, J. F. (1997). "Recombinant *Listeria monocytogenes* Vaccination Eliminates Papillomavirus-Induced Tumors and prevents Papilloma Formation from viral DNA". J. Virol. 71: 8467-8474.

24. Schafer, R., Portnoy, D. A., Brassell, S. A., and Paterson, Y. (1992). "Induction of a cellular immune response to a foreign antigen by a recombinant *Listeria monocytogenes* vaccine". J. Immunol. 149: 53-9.

25. Ikonomadis, G., Paterson, Y., Kos, F. J., and Portnoy, D. A., (1994). "Delivery of a viral antigen to the class I processing and presentation pathway by *Listeria monocytogenes*". J. Exp. Med. 180: 2209-18.

26. Frankel, F. R., Hegde, S., Lieberman, J., and Paterson, Y. (1995). "Induction of cell-mediated immune response to human immunodeficiency virus type 1 Gag protein by using *Listeria monocytogenes* as a live vaccine vector". J. Immunol. 155: 4775-82.

27. Pan, Z. K., Ikonomidis, G., Lazenby, A., Pardoll, D., and Paterson, Y. (1995). "A recombinant *Listeria monocytogenes* vaccine expressing a model tumour antigen protects mice against lethal tumour cell challenge and causes regression of established tumours". Nature Med. 1: 471-7.

28. Dramai, S., Kocks, C., Forestier, C. and Cossart, P. (1993). "Internalin-mediated invasion of epithelial cells by *L. Monocytogenes* is regulated by bacterial growth, temperature and the pleiotropic activator, prfA". Mol. Microbiol. 9: 931-41.

29. Alvarex-Dominguez, C., Vazquez-Boland, J. A., Carrasco-Marin, E., Lopez-Mato, P. and Leyva-Cobian, F. (1997). "Host cell heparan sulfate proteoglycans mediate attachment and entry of *Listeria monocytogenes*, and the listerial surface protein ActA is involved in heparan sulfate receptor recognition". Infect. Immun. 65: 78-88.

30. Domann, E., Wehland, J., Rohde, M., Pistor, S., Hartl, M., Goebel, W., Leimeister-Wächter, M., Wuenscher, M., and Chakraborty, T. (1992). "A novel bacterial virulence gene in *L. monocytogenes* required for host microfilament interaction with homology to the proline rich region of vinculin". EMBO. J. 11: 1981-1990.

31. Kocks, C., Gouin, E., Tabouret, M., Berche, P., Ohayon, M., and Cossart, P. (1992). "*Listeria monocytogenes* induced actin assembly requires the act gene product, a surface protein". Cell 68: 521-31.

32. Armstrong, D., "*Listeria monocytogenes*" (1995) in Principle and Practice of Infectious Diseases, Eds. Mandell, Douglas and Bennett, J. E. and Dolin R., pp. 1880-1885. Churchill Livingstone, New York, 1995.

32a. Boucher, R. C. (1996). "Current status of CF gene therapy". Trends in Genetics 12: 81-84.

32b. Bank, A. (1996). "Human somatic cell gene therapy". BioEssays 18: 999-1007.

33. O'Callaghan, D., Maskell, d., Titi, J., Dougan, G. (1990). "Immune responses in BALB/C mice following immunization with aromatic compound or purine-dependent *Salmonella typhimuriium* strains". Immunology 69: 184-189.

34. Tacket, C. O., Sztein, M. B., Losonsky, G. A., Wasserman, S. S, Nataro, J. P., Edelman, R., Pickard, D., Dougan, G., Chatfiled, S., and Levine, M. M. (1997). "Safety of Live Oral *Salmonella typhi* Vaccine Strains with deletions in htrA and aroC, aroD and immune response in humans". Infect. Immun. 65: 452-456.

35. Curtiss III, R. (1989). "Attenuated *Salmonella* strains as live vectors for the expression of foreign antigens". In New generation vaccines: The molecular approach (ed. M. M. Levine and G. Woodrow), p. 161. Marcel Dekker, New York.

36. Hopkins, S., Kraehenbuhl, J. -P., Schödel, F., Potts, A., Peterson, D., De Grandi, P. and Nardeli-Haeflinger, D. (1995). "A recombinant Salmonella typhimurium vaccine induces local immunity by four different routes of immunization". Infect. Immun. 63: 3279-3286.

37. Berkmen, M., Benedik, M. J., and Blasi, U. (1997). "The *Serratia marescens* NucE protein functions as a holin in *Escherichia coli*". J. Bacterial. 179: 6522-6524.

38. Diaz, E., Munthali, M., de Lorenzo, V., and Timmis, K. N. (1994). "Universal barrier to lateral spread of specific genes among microorganisms". Mol. Microbiol. 13: 855-861.

39. Hohmann, El., Oletta, C. A., Loomis, W. P., and Miller, S. I. (1995). "Macrophage-inducible expression of a model antigen in *Salmonella typhimurium* enhances immunogeneticity". Proc. Natl. Acad. Sci. USA 92: 2904-2908.

40. Park, S. F., and Stewart, G. S. (1990). "High-efficiency transformation of *Listeria monocytogenes* by electroporation of penicillin-treated cells". Gene 94: 129-132.

41. Premaratne, R. J., Lin, W. J., and Johnson, E. A. (1991), "Development of an improved chemically defined minimal medium for *L. monocytogenes*". Appl. Environ. Microbiol. 57: 3046-48.

The invention claimed is:

1. A bacterium for gene transfer to eukaryotic cells comprising:
   a foreign DNA integrated into an episomal vector, wherein the transcription and expression of the foreign DNA is under the control of a eukaryotic regulatory sequence, wherein the bacterium is:
   (i) *L. innocua* comprising a wild-type hly gene from *L. monocytogenes;*
   (ii) *E. coli* comprising a wild-type hly gene from *L. monocytogenes;*
   (iii) *E. coli* strain K12 comprising an inv gene from *Y. pseudotuberculosis;*
   (iv) *Bacillus subtilis* comprising a wild-type hly gene from *L. monocytogenes*
   (v) *L. monocytogenes* comprising a deleted or attenuated cspL, hly, plcB, or dapE gene; or
   (vi) *S. typhimurium* comprising a deleted or attenuated phoP gene.

2. The bacterium of claim 1, wherein the eukaryotic regulatory sequence originates from a previously selected target organ.

3. The bacterium of claim 1, wherein the bacterium further comprises an exogenous suicide gene.

4. The bacterium of claim 1, wherein the bacterium of (i), (ii) or (iv) further comprises a wild-type actA gene from *L. monocytogenes.*

5. A method for the production and extraction of proteins, comprising:
   a) providing a bacterium useful for gene transfer to eukaryotic cells that comprises a foreign DNA integrated into an episomal vector, wherein the transcription and expression of the foreign DNA is under the control of a eukaryotic regulatory sequence and wherein the bacterium is:
   (i) *L. innocua* comprising a wild-type hly gene from *L. monocytogenes;*
   (ii) *E. coli* comprising a wild-type hly gene from *L. monocytogenes;*
   (iii) *E. coli* strain K12 comprising an inv gene from *Y. pseudotuberculosis;*
   (iv) *Bacillus subtilis* comprising a wild-type hly gene from *L. monocytogenes;*
   (v) *L. monocytogenes* comprising a deleted or attenuated cspL, hly, plcB, or dapE gene; or
   (vi) *S. typhimurium* comprising a deleted or attenuated phoP gene;
   b) infecting the eukaryotic somatic cells of the organism with the bacterium to produce transgenic cells, said transgenic cells expressing the foreign DNA to produce a foreign protein encoded by said foreign DNA; and
   c) isolating the foreign protein from the cell, tissue or organ.

6. The method of claim 5, wherein the eukaryotic regulatory sequence originates from a previously selected target organ.

7. The method of claim 5, wherein the bacterium further comprises an exogenous suicide gene.

8. The method of claim 5, wherein the bacteria is of the strain *Listeria monocytogenes* EGH HlyD$_{491A}$, which is deposited at the Deutsche Sammlung von Mikroorganismen und Zellkulturen under the number 11881.

9. The method of claim 5, wherein the bacteria is of the strain *Listeria monocytogenes* and EGD Delta actA Delta plcB, which is deposited at the Deutsche Sammlung von Mikroorganismen und Zellkulturen under the number of 11882.

10. The method of claim 5, wherein the bacteria is of the strain *Listeria monocytogenes* EGD Delta cspL 1, which is deposited at the Deutsche Sammlung von Mikroorganismen und Zellkulturen under the number of 11883.

11. The method of claim 5, wherein the organism is selected from the group consisting of: (a) a domestic animal, with the transgenesis being induced in the blood or other tissues of the domestic animal, (b) a lactating animal, with the transgenesis being induced in the udder of the lactating animal, and (c) a poultry organism, with the transgenesis being induced in eggs of a poultry bird.

12. The method of claim 5 wherein the foreign protein is selected from the group consisting of a hormone, a regulation factor, an enzyme, an enzyme inhibitor and a human monoclonal antibody.

13. The method of claim 5, wherein the bacterium of (i), (ii) or (iv) further comprises a wild-type actA gene from *L. monocytogenes*.

* * * * *

SEQUENCE LISTING

<160> NUMBER OF SEQ ID NOS: 4

<210> SEQ ID NO 1
<211> LENGTH: 1260
<212> TYPE: DNA
<213> ORGANISM: Listeria monocytogenes Strain EGD1/2a
<220> FEATURE:
<221> NAME/KEY: CDS
<222> LOCATION: (241)..(1197)
<223> OTHER INFORMATION: Sequence of the dapE gene, which is essential for synthesis of diaminopimelic acid.

<400> SEQUENCE: 1

```
tgcctttata gagaacggga aaacatagag tggaattcat agaaagaggg cgtgaaatat      60
ggaccaacaa aaaagattc aaattttaaa ggacttggta atattgatt cgactaatgg      120 gcatgaagaa caagttgcga actatttgca aaagttgtta gctgaacatg gtattgagtc      180
cgaaaaggta caatacgacc tagacagagc tagcctagta agcgaaattg gttccagtaa      240 cga gaa ggt ttg gca ttt tca ggg cat atg gat gta gtt gat gcg ggt      288
Arg Glu Gly Leu Ala Phe Ser Gly His Met Asp Val Val Asp Ala Gly
  1               5                  10                  15 gat gta tct aag tgg aag ttc cca cct ttt gaa gcg aca gag cat gaa      336
Asp Val Ser Lys Trp Lys Phe Pro Pro Phe Glu Ala Thr Glu His Glu
             20                  25                  30 ggg aaa cta tac gga cgc ggc gca acg gat atg aag tca ggt cta gcg      384
Gly Lys Leu Tyr Gly Arg Gly Ala Thr Asp Met Lys Ser Gly Leu Ala
         35                  40                  45 gcg atg gtt att gca atg att gaa ctt cat gaa gaa aaa caa aaa cta      432
Ala Met Val Ile Ala Met Ile Glu Leu His Glu Glu Lys Gln Lys Leu
     50                  55                  60 aac ggc aag atc aga tta tta gca aca gtt ggg gaa gag atc ggt gaa      480
Asn Gly Lys Ile Arg Leu Leu Ala Thr Val Gly Glu Glu Ile Gly Glu
 65                  70                  75                  80 ctt gga gca gaa caa cta aca caa aaa ggt tac gca gat gat tta cat      528
Leu Gly Ala Glu Gln Leu Thr Gln Lys Gly Tyr Ala Asp Asp Leu His
                 85                  90                  95 ggt tta atc atc ggc gaa ccg agt gga cac aga atc gtt tat gcg cat      576
Gly Leu Ile Ile Gly Glu Pro Ser Gly His Arg Ile Val Tyr Ala His
            100                 105                 110 aaa ggt tcc att aat tat ccc gtt aaa tcc act ggt aaa aat gcc cat      624
Lys Gly Ser Ile Asn Tyr Pro Val Lys Ser Thr Gly Lys Asn Ala His
        115                 120                 125 agt tcg atg ccg gaa tct ggt gtg aat gcg att gat aac ttg ctg cta      672
Ser Ser Met Pro Glu Ser Gly Val Asn Ala Ile Asp Asn Leu Leu Leu
    130                 135                 140 ttt tat aat gaa gta gaa aaa ttc gtg aaa tca gtt gat gct act aac      720
Phe Tyr Asn Glu Val Glu Lys Phe Val Lys Ser Val Asp Ala Thr Asn
145                 150                 155                 160 gaa ata tta ggc gat ttt att cat aat gtc acc gta att gat ggt gga      768
Glu Ile Leu Gly Asp Phe Ile His Asn Val Thr Val Ile Asp Gly Gly
                165                 170                 175 aat caa gtc aat agt atc cct gaa aaa gca caa ctg caa ggg aat att      816
Asn Gln Val Asn Ser Ile Pro Glu Lys Ala Gln Leu Gln Gly Asn Ile
            180                 185                 190 cgc tcg att cca gaa atg gat aat gaa aca gtg aaa caa gtg cta gtg      864
Arg Ser Ile Pro Glu Met Asp Asn Glu Thr Val Lys Gln Val Leu Val
        195                 200                 205 aag att atc aat aag tta aac aaa cag gaa aat gtg aat ctg gaa tta      912
Lys Ile Ile Asn Lys Leu Asn Lys Gln Glu Asn Val Asn Leu Glu Leu
```

```
                    210                215                220
ata ttt gat tat gat aaa caa cca gta ttt agt gat aaa aat tcg gat          960
Ile Phe Asp Tyr Asp Lys Gln Pro Val Phe Ser Asp Lys Asn Ser Asp
225                 230                 235                 240 tta gtc cac att gct aag agc gta gca agc gac att gtc aaa gaa gaa         1008
Leu Val His Ile Ala Lys Ser Val Ala Ser Asp Ile Val Lys Glu Glu
                    245                 250                 255 atc cca tta ctc ggt att tcc gga aca acc gat gca gca gaa ttt acc         1056
Ile Pro Leu Leu Gly Ile Ser Gly Thr Thr Asp Ala Ala Glu Phe Thr
                    260                 265                 270 aaa gct aag aaa gag ttc cca gtg att att ttt gga cca gga aac gaa         1104
Lys Ala Lys Lys Glu Phe Pro Val Ile Ile Phe Gly Pro Gly Asn Glu
                    275                 280                 285 acc cct cac caa gta aac gaa aat gtt tct ata gga aat tat ttg gag         1152
Thr Pro His Gln Val Asn Glu Asn Val Ser Ile Gly Asn Tyr Leu Glu
                    290                 295                 300 atg gta gat gtt tac aaa cgg att gcc acc gag ttt tta tct tga             1197
Met Val Asp Val Tyr Lys Arg Ile Ala Thr Glu Phe Leu Ser
305                 310                 315 tgaaacttta actttactta tttcccgata taaaataagt aattaataga agtctagtat      1257
ttg                                                                    1260

<210> SEQ ID NO 2
<211> LENGTH: 318
<212> TYPE: PRT
<213> ORGANISM: Listeria monocytogenes Strain EGD1/2a

<400> SEQUENCE: 2

Arg Glu Gly Leu Ala Phe Ser Gly His Met Asp Val Val Asp Ala Gly
 1               5                  10                  15

Asp Val Ser Lys Trp Lys Phe Pro Pro Phe Glu Ala Thr Glu His Glu
                20                  25                  30

Gly Lys Leu Tyr Gly Arg Gly Ala Thr Asp Met Lys Ser Gly Leu Ala
            35                  40                  45

Ala Met Val Ile Ala Met Ile Glu Leu His Glu Glu Lys Gln Lys Leu
        50                  55                  60

Asn Gly Lys Ile Arg Leu Leu Ala Thr Val Gly Glu Glu Ile Gly Glu
65                  70                  75                  80

Leu Gly Ala Glu Gln Leu Thr Gln Lys Gly Tyr Ala Asp Asp Leu His
                85                  90                  95

Gly Leu Ile Ile Gly Glu Pro Ser Gly His Arg Ile Val Tyr Ala His
            100                 105                 110

Lys Gly Ser Ile Asn Tyr Pro Val Lys Ser Thr Gly Lys Asn Ala His
        115                 120                 125

Ser Ser Met Pro Glu Ser Gly Val Asn Ala Ile Asp Asn Leu Leu Leu
130                 135                 140

Phe Tyr Asn Glu Val Glu Lys Phe Val Lys Ser Val Asp Ala Thr Asn
145                 150                 155                 160

Glu Ile Leu Gly Asp Phe Ile His Asn Val Thr Val Ile Asp Gly Gly
                165                 170                 175

Asn Gln Val Asn Ser Ile Pro Glu Lys Ala Gln Leu Gln Gly Asn Ile
            180                 185                 190

Arg Ser Ile Pro Glu Met Asp Asn Glu Thr Val Lys Gln Val Leu Val
        195                 200                 205

Lys Ile Ile Asn Lys Leu Asn Lys Gln Glu Asn Val Asn Leu Glu Leu
    210                 215                 220
```

```
Ile Phe Asp Tyr Asp Lys Gln Pro Val Phe Ser Asp Lys Asn Ser Asp
225                 230                 235                 240

Leu Val His Ile Ala Lys Ser Val Ala Ser Asp Ile Val Lys Glu Glu
            245                 250                 255

Ile Pro Leu Leu Gly Ile Ser Gly Thr Thr Asp Ala Ala Glu Phe Thr
                260                 265                 270

Lys Ala Lys Lys Glu Phe Pro Val Ile Ile Phe Gly Pro Gly Asn Glu
            275                 280                 285

Thr Pro His Gln Val Asn Glu Asn Val Ser Ile Gly Asn Tyr Leu Glu
        290                 295                 300

Met Val Asp Val Tyr Lys Arg Ile Ala Thr Glu Phe Leu Ser
305                 310                 315

<210> SEQ ID NO 3
<211> LENGTH: 1337
<212> TYPE: DNA
<213> ORGANISM: Listeria monocytogenes Strain EGD1/2a
<220> FEATURE:
<221> NAME/KEY: CDS
<222> LOCATION: (795)..(992)
<223> OTHER INFORMATION: Sequence of cold shock protein cspL

<400> SEQUENCE: 3
gaggcaagtg gactaatcat aaagtttttg gcgatgcaac tgcgattttg gcaggagatg      60
ctttactaac gctcgctttt tctatttttag ctgaagacga taatttatct tttgagacac     120
gcattgcttt gattaaccaa attagtttta gtagcggtgc agaaggaatg gttggtggtc     180
aacttgcaga cttggaagcg gaaaacaaac aagtgacgct agaagagtta tcatccattc     240
atgcacgaaa aacgggtgaa ttattaattt atgctgtaac ctctgcagca aaaattgcgg     300
aagctgatcc agaacaaacg aaacgcttac gaattttttgc agagaatatt gggattggat     360
ttcaaattag cgacgatatt ttagatgtaa ttggtgatga aacgaaaatg ggtaaaagaa     420
caggggccga cgcttttctg aataaaagta cctatcccgg attactcacg cttgatgggg     480
caaaaagggc attaaatgag catgttacga ttgcaaagtc agcgctttca gggcatgatt     540
tcgatgatga aattctcttg aaacttgctg atttaatcgc acttagagaa aattaatcat     600
aattatctag taatttcaaa attttttcac atatataatt caaattgatt tgcttttcct     660
aaaataccgt gttatactaa tgtaagatta ttttttgtggg tgaaagatac gattgtgaac     720
aactttccat ctcgtgccgt taagcaagaa tagtaaataa ttagtgtgca taacacacga     780
ggaggaacat gaac atg gaa caa ggt aca gta aaa tgg ttt aac gca gaa         830
              Met Glu Gln Gly Thr Val Lys Trp Phe Asn Ala Glu
                1               5                   10 aaa gga ttt ggt ttt atc gaa cgc gaa aac ggt gac gat gta ttc gta         878
Lys Gly Phe Gly Phe Ile Glu Arg Glu Asn Gly Asp Asp Val Phe Val
        15                  20                  25 cat ttc agc gct atc caa ggc gac gga ttc aaa tct tta gac gaa ggt         926
His Phe Ser Ala Ile Gln Gly Asp Gly Phe Lys Ser Leu Asp Glu Gly
    30                  35                  40 caa gca gta act ttc gac gtt gaa gaa ggc caa cgc gga cct caa gca         974
Gln Ala Val Thr Phe Asp Val Glu Glu Gly Gln Arg Gly Pro Gln Ala
45                  50                  55                  60 gct aac gtt caa aaa gcg taattctatt ttttgaataa gaaaaagcaa              1022
Ala Asn Val Gln Lys Ala
                65 atcatttcgg tgatttgctt ttttatttgt ctaaaattat tttaccttgt ttggtttaat      1082
```

-continued

```
ggcgattgtt tgctataata agaacaatta atcgagaaaa aagaccttgc acgcattcat    1142
gcgagtggct ctttggaaag tgagttgttt ttatttggat cttttaaaga taaaggatcc    1202
ttcctttatg aagcgattgg atatacaaga attagaagca cttgcagcgg atattcgcgc    1262
ttttttaatt acttctacat ctaaatcagg tgggcatatt ggtccgaatc ttggtgtggt    1322
agaactaacg attgc                                                    1337
```

<210> SEQ ID NO 4
<211> LENGTH: 66
<212> TYPE: PRT
<213> ORGANISM: Listeria monocytogenes Strain EGD1/2a

<400> SEQUENCE: 4

```
Met Glu Gln Gly Thr Val Lys Trp Phe Asn Ala Glu Lys Gly Phe Gly
 1               5                  10                  15

Phe Ile Glu Arg Glu Asn Gly Asp Asp Val Phe Val His Phe Ser Ala
             20                  25                  30

Ile Gln Gly Asp Gly Phe Lys Ser Leu Asp Glu Gly Gln Ala Val Thr
         35                  40                  45

Phe Asp Val Glu Glu Gly Gln Arg Gly Pro Gln Ala Ala Asn Val Gln
     50                  55                  60

Lys Ala
 65
```